United States Patent [19]

Jakupovic et al.

[11] Patent Number: 6,017,959
[45] Date of Patent: Jan. 25, 2000

[54] FORMS OF ORGANIC SALTS OF N,N'-DIACETYLCYSTINE

[75] Inventors: Edib Jakupovic, Nykvarn; Eric Teneberg, Älvsjö, both of Sweden

[73] Assignee: Astra Aktiebolag, Sodertalje, Sweden

[21] Appl. No.: 08/981,404

[22] PCT Filed: Jun. 17, 1997

[86] PCT No.: PCT/SE97/01069

§ 371 Date: Dec. 18, 1997

§ 102(e) Date: Dec. 18, 1997

[87] PCT Pub. No.: WO97/48679

PCT Pub. Date: Dec. 24, 1997

Related U.S. Application Data

[63] Continuation of application No. PCT/SE97/01069, Jun. 17, 1997.

[30] Foreign Application Priority Data

Jun. 18, 1996 [SE] Sweden .................................. 9602416

Jun. 18, 1996 [SE] Sweden .................................. 9602419

[51] Int. Cl.$^7$ ...................... C07C 323/59; A61K 31/195; A61K 31/225

[52] U.S. Cl. ........................... 514/554; 514/562; 562/557

[58] Field of Search .................................. 514/554, 562; 562/557

[56] References Cited

U.S. PATENT DOCUMENTS 5,385,904 1/1995 Andersson et al. ..................... 514/255

*Primary Examiner*—Frederick Krass
*Attorney, Agent, or Firm*—Fish & Richardson, P.C.

[57] ABSTRACT

New hydrated salts of N,N'-diacetylcystine are described, as well as processes for the preparation thereof.

39 Claims, No Drawings

FORMS OF ORGANIC SALTS OF N,N'-DIACETYLCYSTINE

This is a continuation of International Patent Application No. PCT/SE97/01069, with an international filing date of Jun. 17, 1997, now pending.

The present invention relates to new hydrates of salts of N,N-diacetylcystine and to processes for the preparation thereof.

BACKGROUND OF THE INVENTION

N-acetyl-L-cysteine is a well-known compound which is used as a therapeutic agent against chronic obstructive pulmonary diseases and chronic bronchitis. Although the first patent was filed in 1964 (GB 954268), the mechanism of action of the compound has not been established. It is also known that the corresponding disulphide of N-acetyl-L-cysteine, i.e., N,N-diacetyl-L-cystine, L-DiNAC, acts as a potent immunostimulator (SE patent application No. 9002067-8), showing an activity comparable to contemporary immunostimulants such as sodium diethyl dithiocarbamate or 2,2'-dithiobisethanol.

It has recently been found that certain salts of DiNAC with organic bases exhibit a favourable combination of non-hygroscopicity and crystallinity which permits the isolation and formulation of these salts in solid form. They have the advantages of ease of crystallisation, non-hygroscopicity and chemical stability, as well as the immunomodulating activity of DiNAC, and are thus medically useful. These salts are described in WO 93/11104.

Salts composed of an organic base and N,N-diacetylcystine (DiNAC) are generally prepared by mixing DiNAC and the organic base, as defined above, each dissolved or dispersed in a solvent or solvent mixture. Solvents, such as water, alcohols, glycols, ketones, amides, sulphoxides or other polar solvents may be used; solvent mixtures may also be used. The salt either precipitates directly from the reaction mixture, or is obtained by the addition of a less polar solvent, by evaporation, or by lyophilisation. The reaction is performed at elevated temperature or room temperature, depending on the solubility in the medium. Alternatively, the salt can be prepared by oxidation of the appropriate N-acetyl cysteine salt in an aqueous or alcoholic solution, followed by precipitation as above. The oxidation may be effected either chemically, using, e.g., hydrogen peroxide or a halogen, or electrochemically.

The above methods provide the organic salts of DiNAC in anhydrous form.

DISCLOSURE OF THE INVENTION

We have now prepared novel hydrates of certain salts of N,N'-diacetylcystine. The invention, in one aspect, provides hydrated salts of N,N'-diacetylcystine, having the formula

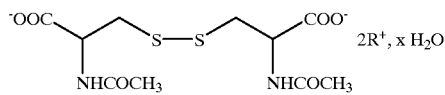

in which
the N,N'-diacetylcystine is the D-, L-, or meso form, or any mixture thereof,
R$^+$ is the protonated form of lysine, ammonia or N-benzyl-2-phenylethylamine, and
x is 1, 1.5, or 2, designating the monohydrate, sesquihydrate, and dihydrate, respectively, provided that when, and only when, R$^+$ is the protonated form of N-benzyl-2-phenylethylamine, x is 1.5.

The N,N'-diacetylcystine is preferably the L-form. The lysine is preferably L-lysine.

In another aspect, the invention provides a process for obtaining the hydrated salts. The process includes oxidising N-acetyl cysteine in the presence of lysine, ammonia or N-benzyl-2-phenylethylamine, or the protonated forms thereof, in an aqueous or alcoholic solution, preferably in the presence of a catalytic amount of an alkali metal hydroxide, and crystallising the hydrate using a solvent comprising an alcohol or a ketone, preferably ethanol or acetone.

When the hydrated salt is a dihydrate, or the sesquihydrate, the crystallisation is carried out using a solvent comprising an alcohol, preferably ethanol. When the hydrated salt is the lysinium monohydrate, the crystallisation is carried out using a solvent comprising an alcohol, preferably ethanol, and when the hydrated salt is the ammonium monohydrate, the crystallisation is carried out using a solvent comprising a ketone, preferably acetone.

When the hydrated salt is a dihydrate, or the sesquihydrate, the crystallisation is carried out using a solvent comprising an alcohol, preferably ethanol. When the hydrated salt is the lysinium monohydrate, the crystallisation is carried out using a solvent comprising an alcohol, preferably ethanol, and when the hydrated salt is the ammonium monohydrate, the crystallisation is carried out using a solvent comprising a ketone, preferably acetone.

Specifically, the hydrated forms of di-lysinium-N,N'-diacetylcystinate may be prepared for example by oxidising N-acetyl cysteine in an aqueous or alcoholic solution in the presence of lysine or a salt containing the protonated form of lysine, and a catalytic amount of an alkali metal hydroxide, and then a) to obtain the monohydrated lysine salt, crystallising the product by adding an aqueous solution thereof to ethanol, preferably at a temperature of about 45° C.;

b) to obtain the dihydrated salt, crystallising the product by adding ethanol to an aqueous solution thereof at a temperature of about 60° C. or below, or by adding an aqueous solution of the product to a mixture of ethanol and water at a temperature of below about 60° C., for example at about 20° C. or below.

The monohydrate form of the lysine salt of N,N'-diacetylcystine is metastable, while the dihydrate form is stable and especially suitable for use in inhalation devices.

The hydrated forms of di-ammonium-N,N'-diacetylcystinate may be prepared for example by oxidising N-acetyl cysteine in an aqueous solution in the presence of ammonia or ammonium hydroxide, or in the presence of another salt containing the protonated form of ammonia and a catalytic amount of an alkali metal hydroxide, and a) to obtain the monohydrated salt, crystallising the product by adding acetone b) to obtain the dihydrated salt, crystallising the product by adding ethanol to an aqueous solution thereof.

Crystallisation of the dihydrated ammonium salt as above is preferably carried out at a temperature of for example between about 40° C. and about 80° C., preferably between about 40° C. and about 78° C., for example at about 78° C.

An alternative method of crystallising the dihydrated ammonium salt involves adding the oxidised product to a mixture of ethanol and water.

Di-N-benzyl-2-phenylethylamine sesquihydrate may be prepared for example by oxidising N-acetyl cysteine in an aqueous or alcoholic solution in the presence of N-benzyl-2-phenylethylamine or a salt containing the protonated form of N-benzyl-2-phenylethylamine, and a catalytic amount of an alkali metal hydroxide, and then adding ethanol and standing at 0–5° C. to crystallise.

By "catalytic amount" is meant a trace amount of alkali metal hydroxide; preferably at least 0.001 mole equivalent compared to the N-acetyl-L-cysteine is used, or up to 0.01 or 0.1 mole equivalent. Preferably no more than 0.5 mole equivalent is used. In one embodiment of the invention, about 0.1 mole equivalent of the alkali metal hydroxide is used.

Suitable alkali metal hydroxides are, e.g., sodium, potassium and lithium hydroxide.

The oxidation may be effected either chemically, using, e.g., hydrogen peroxide or halogen as oxidising agent, or electrochemically.

The hydrated salts of the present invention have immunomodulating activity and may be used for example in the treatment of diseases where an anergy of the immune response or an aberrant immune response or an ineffective host response can be suspected. Among such diseases are included the diseases listed in WO 93/11104, incorporated herein by reference. For example, diseases which may benefit from treatment with the present hydrated salts include chronic bronchitis, malignant diseases and chronic infections. The ability of the hydrated salts to modulate immune responses may be illustrated in the animal delayed type hypersensitivity (DTH) test in the mouse, as described in WO 93/11104. The present hydrated salts will also be useful in the treatment of chronic hepatitis B and/or C infections, as may be illustrated by a strengthening of the TH1-type response in the Leishmania model, as described for example by Connell et al ((N. Connell, E. Medina-Acosta, W. McMaster, B. Bloom and D. Russell, 1993, Effective immunisation against cutaneous leishmaniasis with recombinant bacilli Calmette-Guerin expressing the Leishmania surface proteinase p63, Proc. Natl. Acad. Sci. USA, 90:11473).

The new hydrated salts can be formulated for administration by inhalation, for example from a dry powder inhaler or from a pressurised metered dose inhaler (pMDI); alternatively, they can be formulated for oral, topical, or parenteral use. The formulations may include a pharmaceutically acceptable carrier.

The hydrated salts of the present invention can be included in different dosage forms, e.g., dry powders, aerosols, tablets, coated tablets, gelatine capsules and solutions.

For the preparation of a formulation for inhalation from a dry powder inhaler, the hydrated salts of the present invention may be combined with for example a pharmaceutically acceptable diluent or carrier and provided in the form of inhalable particles.

For the preparation of a formulation for inhalation from a pMDI the hydrated salts of the present invention may be dissolved or suspended in a suitable propellant optionally together with a co-solvent and/or one or more pharmaceutically acceptable surfactants or other excipients.

For the preparation of tablets, coated tablets and gelatine capsules the hydrated salts of the present invention can be combined with pharmaceutically acceptable materials, e.g., lactose, starch, dicalcium phosphate, microcrystalline cellulose, polyvinylpyrrolidone, gelatine, cellulose derivatives, colloidal silicone dioxide, talc and stearic acid or its salts.

For the preparation of oral solutions suitable excipients are water, saccharose, glucose, sorbitol, fructose and xylitol.

The dosage forms can besides mentioned excipients contain preservatives, stabilisers, viscosity regulating agents, emulsifiers, sweetening agents, colouring agents, flavouring agents, tonicity regulating agents, buffers or antioxidants. They can also contain other therapeutically valuable substances.

The invention is illustrated by the following non-limiting examples.

EXAMPLE 1

Di-L-lysinium-N,N'-diacetyl-L-cystinate monohydrate

N-acetyl-L-cysteine (50.0 g, 1.0 eq), L-lysine monohydrate (50.5 g, 1.0 eq), potassium hydroxide (1.6 g, 0.08 eq) and purified water (75 mL) were mixed and stirred until a clear solution was achieved. Hydrogen peroxide, (35% solution, 0.5 eq) was then added dropwise, with the temperature kept between about 20° C. and about 40° C. during the addition. The solution was heated to 45° C., and ethanol (1500 mL) was added. After stirring at 45° C. for one hour, the crystals were filtered off, giving 71 g (70%) of the title substance.

The $^1$H-NMR and $^{13}$C-NMR spectra showed the following peaks:

$^1$H-NMR (D$_2$O): δ4.50 (dd, 2H), 3.75 (t, 2H), 3.26 (dd, 2H), 3.03 (t, 4H), 2.96 (dd, 2H), 2.06 (s, 6H), 1.84–1.96 (m, 4H), 1.73 (quintet, 4H), 1.35–1.60 (m, 4H).

$^{13}$C-NMR (D$_2$O): δ177.6, 175.5, 174.4, 67.3, 55.2, 54.9, 40.7, 39.8, 30.7, 27.2, 22.7, 22.2.

Powder X-ray diffractograms of the product, measured from 1 to 40° in 2θ showed the following peaks, which are characteristic of the monohydrate:

| Angle [°2θ] | d-value CuKα$^1$ [Å] | Intensity |
|---|---|---|
| 4.68 | 18.87 | strong |
| 5.30 | 16.66 | strong |
| 6.54 | 13.50 | very strong |
| 7.50 | 11.79 | very strong |
| 10.56 | 8.37 | strong |
| 13.97 | 6.33 | strong |
| 14.24 | 6.21 | strong |
| 18.66 | 4.75 | strong |
| 19.46 | 4.56 | strong |
| 20.15 | 4.40 | very strong |
| 21.17 | 4.19 | strong |
| 22.33 | 3.98 | strong |
| 22.59 | 3.93 | strong |
| 22.81 | 3.90 | strong |
| 23.05 | 3.86 | strong |
| 23.38 | 3.80 | strong |
| 23.80 | 3.74 | strong |

Karl-Fischer-titration showed 2.8% (w/w) of water which is equivalent to the theoretical value.

EXAMPLE 2

Di-L-lysinium-N,N'-diacetyl-L-cystinate dehydrate

N-acetyl-L-cysteine (50.0 g, 1.0 eq), L-lysine monohydrate (50.5 g, 1.0 eq), potassium hydroxide (1.6 g, 0.08 eq) and purified water (75 mL) were mixed and stirred until a clear solution was achieved. Hydrogen peroxide, (35% solution, 0.5 eq) was then added dropwise, with the temperature kept between about 20° C. and about 40° C. during the addition.

The dihydrate was then crystallised from the above solution, using each of the following methods:

1). The solution was added to 800 ml of ethanol at 60° C. After 3 h of stirring, the crystals were filtered off, giving 74 g (70%) of the title substance.

2). The solution was added to 800 ml of ethanol, containing 10% of water, at 20° C. After 10 h of stirring, the crystals were filtered off, giving 66.5 g (63%) of the title substance. The $^1$H-NMR and $^{13}$C-NMR were identical to those of the monohydrate.

Powder X-ray diffractograms of the product measured from 1 to 40° in 2θ show the following peaks, characteristic of the dihydrate:

| Angle [°2θ] | d-value CuKα$^1$ [Å] | Intensity |
|---|---|---|
| 9.44 | 9.36 | very strong |
| 10.93 | 8.09 | strong |
| 16.70 | 5.31 | strong |
| 17.38 | 5.10 | strong |
| 17.62 | 5.03 | strong |
| 17.99 | 4.93 | very strong |
| 20.01 | 4.43 | strong |
| 21.95 | 4.05 | strong |
| 22.66 | 3.92 | strong |
| 24.11 | 3.69 | strong |
| 24.34 | 3.65 | strong |
| 24.64 | 3.61 | strong |
| 25.27 | 3.52 | very strong |
| 25.93 | 3.43 | strong |

Karl-Fischer-titration showed 5.5% (w/w) of water which is equivalent to the theoretical value.

EXAMPLE 3
Di-ammonium-N,N'-diacetyl-L-cystinate, monohydrate

N-acetyl-L-cysteine (50 g, 1.0 eq.) and purified water (42 mL) were stirred for 15 minutes. Ammonium hydroxide (25% solution, 24 mL, 1.15 eq.) was added dropwise over 20 minutes. To the resulting clear solution was added hydrogen peroxide (14.6 mL, 1.0 eq) over a period of 30 minutes, maintaining a temperature not over 50° C. Acetone (190 mL) was added slowly (over 30 minutes), resulting in crystallisation. The slurry was allowed to stand with stirring at 0° C. for 16 h and the crystals were then filtered off, washed with acetone. (10 mL) and dried, giving 28.8 g (51%) of the title substance.

The XRD values of the monohydrate were as follows:

| Angle [°2θ] | d-value CuKα$^1$ [Å] | Intensity |
|---|---|---|
| 6.00 | 14.73 | weak |
| 9.31 | 9.49 | very weak |
| 11.48 | 7.71 | medium |
| 11.99 | 7.37 | very strong |
| 13.97 | 6.34 | very weak |
| 18.01 | 4.92 | medium |
| 18.51 | 4.79 | very weak |
| 18.77 | 4.73 | very weak |
| 19.39 | 4.58 | weak |
| 20.57 | 4.31 | weak |
| 22.21 | 4.00 | weak |
| 22.78 | 3.90 | weak |
| 23.04 | 3.86 | medium |
| 23.86 | 3.73 | weak |
| 25.15 | 3.54 | medium |
| 25.91 | 3.44 | weak |
| 27.71 | 3.22 | very weak |
| 28.14 | 3.17 | very weak |
| 28.84 | 3.09 | very weak |
| 30.24 | 2.95 | weak |
| 33.57 | 2.67 | very weak |
| 34.16 | 2.62 | very weak |
| 34.85 | 2.57 | very weak |
| 36.45 | 2.46 | very weak |

EXAMPLE 4
Di-ammonium-N,N'-diacetyl-L-cystinate dehydrate

N-acetyl-L-cysteine (50 g, 1.0 eq.) and purified water (42 mL) were stirred for 15 minutes. Ammonium hydroxide (25% solution, 24 mL, 1.15 eq.) was added dropwise over 20 minutes. To the resulting clear solution was added hydrogen peroxide (14.6 mL, 1.0 eq) over a period of 30 minutes, maintaining a temperature not over 50° C. The solution was then slowly added to ethanol (170 mL) at 40–78° C., over 45 minutes. After the addition the temperature was decreased to 0–5° C., resulting in precipitation of crystals. Filtration, washing with ethanol (20 mL) and drying gave 12.9 g (22%) of the title substance.

The XRD values of the monohydrate were as follows:

| Angle [°2θ] | d-value CuKα$^1$ [Å] | Intensity |
|---|---|---|
| 6.28 | 14.06 | weak |
| 7.40 | 11.94 | weak |
| 7.67 | 11.52 | medium |
| 11.63 | 7.61 | medium |
| 13.61 | 6.50 | weak |
| 13.88 | 6.38 | very weak |
| 14.61 | 6.06 | very weak |
| 14.86 | 5.96 | very weak |
| 15.02 | 5.90 | very weak |
| 15.60 | 5.68 | very weak |
| 15.87 | 5.58 | weak |
| 17.15 | 5.17 | weak |
| 18.69 | 4.75 | medium |
| 19.13 | 4.64 | weak |
| 22.20 | 4.00 | medium |
| 23.96 | 3.71 | very weak |
| 24.35 | 3.65 | very weak |

EXAMPLE 5
Di-N-benzyl-2-phenylethylaminium-N,N'-diacetyl-L-cystinate, sesquihydrate N-acetyl-L-cysteine (50 g, 1.0 eq), purified water (75 mL), potassium hydroxide (1.8 g, 0.1 eq) and N-benzyl-2-phenylethylamine (64.6 g, 2.0 eq) were mixed at approx. 25° C. To the mixture was added hydrogen peroxide with cooling to maintain the reaction temperature at 25–30° C. Ethanol (177 mL) was then added and the resulting mixture was allowed to stand overnight at 0–5° C. to crystallise. The obtained crystals were filtered off, washed with ethanol (50 mL) and dried to give 17.2 g (10%) of the title compound.

The XRD values for the sesquihydrate were as follows.

| Angle [°2θ] | d-value CuKα$^1$ [Å] | Intensity |
|---|---|---|
| 6.20 | 14.26 | strong |
| 9.63 | 9.18 | strong |
| 10.01 | 8.83 | medium |
| 12.42 | 7.12 | very weak |
| 12.78 | 6.92 | weak |
| 13.61 | 6.50 | medium |
| 14.92 | 5.93 | weak |
| 15.22 | 5.82 | weak |
| 15.83 | 5.59 | very weak |
| 16.54 | 5.36 | medium |
| 17.35 | 5.11 | weak |
| 18.67 | 4.75 | strong |
| 19.26 | 4.60 | strong |
| 20.49 | 4.33 | strong |
| 20.83 | 4.26 | medium |
| 21.47 | 4.14 | strong |

| Angle [°2θ] | d-value CuKα¹ [Å] | Intensity |
|---|---|---|
| 21.82 | 4.07 | medium |
| 22.05 | 4.03 | medium |
| 23.18 | 3.83 | medium |
| 23.85 | 3.73 | very weak |
| 24.23 | 3.67 | medium |
| 25.68 | 3.47 | very weak |
| 26.01 | 3.42 | very weak |
| 26.11 | 3.41 | very weak |
| 27.89 | 3.20 | medium |
| 29.16 | 3.06 | weak |
| 31.08 | 2.88 | very weak |
| 33.12 | 2.70 | very weak |
| 33.49 | 2.67 | very weak |
| 35.19 | 2.55 | very weak |
| 36.20 | 2.48 | very weak |
| 37.44 | 2.40 | very weak |

The X-ray diffractograms also contained several medium, weak and very weak peaks which have been omitted for clarity.

We claim:

1. A hydrated salt of N,N'-diacetylcystine, wherein the hydrated salt has the formula

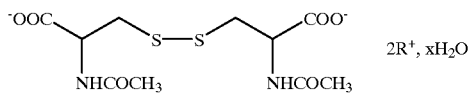

2R⁺, xH₂O in which
the N,N'-diacetylcystine is the D-, L-, or meso form, or any mixture thereof, R⁺ is the protonated form of lysine, and x is 2, designating the dihydrate.

2. A hydrated salt as claimed in claim 1, in which the N,N'-diacetylcystine is the L-form.

3. A hydrated salt as claimed in claim 1, wherein said salt is di-L-lysinium N,N'-diacetyl-L-cystinate dihydrate.

4. A process for the preparation of a hydrated salt of N,N'-diacetylcystine, wherein the hydrated salt has the formula

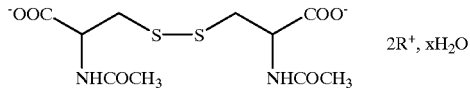

2R⁺, xH₂O in which
the N,N'-diacetylcystine is the D-, L-, or meso form, or any mixture thereof, R⁺ is the protonated form of lysine designating the dihydrate, said process, comprising
a) providing a first solution comprising i) N-acetyl cysteine, ii) lysin or the protonated form thereof, iii) a solvent, wherein the solvent is water or alcohol, and iv) optionally a catalytic amount of an alkali metal hydroxide;
(b) applying an oxidant to the solution; and
(c) adding to the first solution a second solution comprising ethanol, or adding the first solution to a second solution comprising a mixture of ethanol and water, wherein R⁺ is the protonated form of lysine and x is 2.

5. A therapeutic composition comprising as active ingredient a hydrated salt as claimed in claim 1.

6. A therapeutic composition as claimed in claim 5, formulated for administration by inhalation from a dry powder inhaler.

7. Di-ammonium-N,N'-diacetyl-L-cystinate monohydrate.

8. Di-ammonium-N,N'-diacetyl-L-cystinate dihydrate.

9. A method for the treatment of a disease involving an anergy of the immune response, an aberrant immune response or an ineffective immune response in a mammal, said method comprising administering to the mammal a therapeutically effective amount of the hydrated salt of claim 1.

10. A method for the treatment of chronic bronchitis in a mammal, said method comprising administering to the mammal a therapeutically effective amount of the hydrated salt of claim 1.

11. A method for the treatment of a malignant disease in a mammal, said method comprising administering to the mammal a therapeutically effective amount of the hydrated salt of claim 1.

12. A method for the treatment of a chronic infection in a mammal, said method comprising administering to the mammal a therapeutically effective amount of the hydrated salt of claim 1.

13. A method for the treatment of a chronic hepatitis B or C viral infection in a mammal, said method comprising administering to the mammal a therapeutically effective amount of the hydrated salt of claim 1.

14. A therapeutic composition comprising as an active ingredient the hydrated salt of claim 2.

15. A therapeutic composition comprising as an active ingredient the hydrated salt of claim 3.

16. A therapeutic composition as claimed in claim 14, formulated for administration by inhalation from a dry powder inhaler.

17. A therapeutic composition as claimed in claim 15, formulated for administration by inhalation from a dry powder inhaler.

18. A method for the treatment of a disease involving an anergy of the immune response, an aberrant immune response or an ineffective immune response in a mammal, said method comprising administering to the mammal a therapeutically effective amount of the hydrated salt of claim 2.

19. A method for the treatment of a disease involving an anergy of the immune response, an aberrant immune response or an ineffective immune response in a mammal, said method comprising administering to the mammal a therapeutically effective amount of the hydrated salt of claim 3.

20. A method for the treatment of chronic bronchitis in a mammal, said method comprising administering to the mammal a therapeutically effective amount of the hydrated salt of claim 2.

21. A method for the treatment of chronic bronchitis in a mammal, said method comprising administering to the mammal a therapeutically effective amount of the hydrated salt of claim 3.

22. A method for the treatment of a malignant disease in a mammal, said method comprising administering to the mammal a therapeutically effective amount of the hydrated salt of claim 2.

23. A method for the treatment of a malignant disease in a mammal, said method comprising administering to the mammal a therapeutically effective amount of the hydrated salt of claim 3.

24. A method for the treatment of a chronic infection in a mammal, said method comprising administering to the mammal a therapeutically effective amount of the hydrated salt of claim 2.

25. A method for the treatment of a chronic infection in a mammal, said method comprising administering to the mammal a therapeutically effective amount of the hydrated salt of claim 3.

26. A method for the treatment of a chronic hepatitis B or C viral infection in a mammal, said method comprising administering to the mammal a therapeutically effective amount of the hydrated salt of claim 2.

27. A method for the treatment of a chronic hepatitis B or C viral infection in a mammal, said method comprising administering to the mammal a therapeutically effective amount of the hydrated salt of claim 3.

28. A hydrated salt of N,N'-diacetylcystine, wherein the hydrated salt has the formula

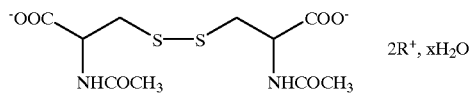

in which
the N,N'-diacetylcystine is the D-, L-, or meso form, or any mixture thereof, R$^+$ is the protonated form of ammonia and x is 1, 1.5, or 2, designating the monohydrate, sesquihydrate, and dihydrate, respectively.

29. A hydrated salt as claimed in claim 28, in which the N,N'-diacetylcystine is the L-form.

30. A process for the preparation of a hydrated salt of N,N'-diacetylcystine, wherein the hydrated salt has the formula

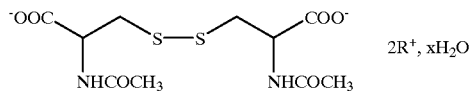

in which
the N,N'-diacetylcystine is the D-, L-, or meso form, or any mixture thereof, R$^+$ is the protonated form of ammonia and x is 1, 1.5, or 2, designating the monohydrate, sesquihydrate, and dehydrate, respectively, comprising
(a) providing a first solution comprising i) N-acetyl cystine, ii) ammonia or the protonated form thereof, iii) a solvent, wherein the solvent is water or alcohol, and
iv) optionally a catalytic amount of an alkali metal hydroxide;
(b) applying an oxidant to the solution; and
(c) (i) adding to the first solution a second solution, wherein the second solution comprises acetone, R$^+$ is the protonated form of ammonia, and x is 1; or (ii) adding to the first solution a second solution comprising ethanol, or adding the first solution to a second solution comprising a mixture of ethanol and water, wherein R$^+$ is the protonated form of ammonia and x is 2.

31. The process of claim 4, wherein step (c)(i) is followed.

32. The process of claim 4, wherein step (c)(ii) is followed.

33. A therapeutic composition comprising as active ingredient a hydrated salt as claimed in claim 28.

34. A therapeutic composition as claimed in claim 28, formulated for administration by inhalation from a dry powder inhaler.

35. A method for the treatment of a disease involving an anergy of the immune response, an aberrant immune response or an ineffective immune response in a mammal, said method comprising administering to the mammal a therapeutically effective amount of the hydrated salt of claim 28.

36. A method for the treatment of chronic bronchitis in a mammal, said method comprising administering to the mammal a therapeutically effective amount of the hydrated salt of claim 28.

37. A method for the treatment of a malignant disease in a mammal, said method comprising administering to the mammal a therapeutically effective amount of the hydrated salt of claim 28.

38. A method for the treatment of a chronic infection in a mammal, said method comprising administering to the mammal a therapeutically effective amount of the hydrated salt of claim 29.

39. A method for the treatment of a chronic hepatitis B or C viral infection in a mammal, said method comprising administering to the mammal a therapeutically effective amount of the hydrated salt of claim 28.

* * * * *